(12) United States Patent
Hamilton et al.

(10) Patent No.: US 6,415,672 B1
(45) Date of Patent: Jul. 9, 2002

(54) INDUSTRIAL DIAGNOSTIC GAUGES FOR READING IN NO LIGHT AND LOW LIGHT CONDITIONS AND METHODS OF READING SAME

(76) Inventors: Michael G. Hamilton, 10134 Sagedale, Houston, TX (US) 77089; Sam M. Ditta, 125 Woodridge, Alvin, TX (US) 77511

( * ) Notice: Subject to any disclaimer, the term of this patent is extended or adjusted under 35 U.S.C. 154(b) by 0 days.

(21) Appl. No.: 09/847,027

(22) Filed: May 1, 2001

Related U.S. Application Data

(63) Continuation-in-part of application No. 09/711,112, filed on Nov. 9, 2000.

(51) Int. Cl.[7] .............................................. G01D 11/28
(52) U.S. Cl. ..................................................... 73/866.3
(58) Field of Search ................................ 73/866.3, 499; 116/202, 284–305, 310, DIG. 6, DIG. 35, DIG. 36; 359/515, 527; 362/23, 25, 28; 374/187, 188, 205–207

(56) References Cited

U.S. PATENT DOCUMENTS

| | | | | |
|---|---|---|---|---|
| 2,707,931 A | * | 5/1955 | Boat et al. | |
| 3,033,035 A | * | 5/1962 | Snodgrass | |
| 3,254,534 A | * | 6/1966 | Graham | |
| 3,453,883 A | * | 7/1969 | Caggia | |
| 4,004,546 A | | 1/1977 | Harland | |
| 4,561,042 A | | 12/1985 | Wehner | |
| 5,439,169 A | * | 8/1995 | Rabel | |

* cited by examiner

Primary Examiner—Robert Raevis
(74) Attorney, Agent, or Firm—Anthony F. Matheny; Andrews & Kurth L.L.P.

(57) ABSTRACT

The invention is directed to industrial diagnostic gauges that are utilized in industrial applications. Examples include pressure and temperature gauges utilized in petrochemical plants. The industrial diagnostic gauges include luminescent materials and reflective materials to facilitate accurate reading of the industrial diagnostic gauges in low and no light conditions from distances greater than 4 feet. Broadly, the industrial diagnostic gauges include a housing, a diagnostic member, a face, at least one hand operatively associated with the diagnostic member, a clear window and a retaining ring. The face may include at least one luminescent material and the at least one marking and the at least one hand each may include at least one reflective material. Additionally, the housing may include at least one marking having either at least one luminescent material or at least one reflective material. Methods of reading industrial diagnostic gauges and methods of manufacturing industrial diagnostic gauges are also disclosed.

20 Claims, 1 Drawing Sheet

INDUSTRIAL DIAGNOSTIC GAUGES FOR READING IN NO LIGHT AND LOW LIGHT CONDITIONS AND METHODS OF READING SAME

CROSS REFERENCE TO RELATED APPLICATIONS

This application is a continuation-in-part of U.S. application Ser. No. 09/711,112, filed Nov. 9, 2000.

BACKGROUND OF THE INVENTION

1. Field of the Invention

The invention is directed to diagnostic gauges that are utilized in industrial applications, and in particular, to diagnostic gauges utilized in industrial locations that can be viewed and read in low and no light conditions.

2. Description of Related Art

Industrial diagnostic gauges, or diagnostic gauges, are required in numerous industrial applications. Many of these applications require the diagnostic gauges to be placed in locations that are difficult for a person to access. For example, a diagnostic gauge may be located in a radioactive or other hazardous location, e.g., nuclear power plants, biohazard laboratories; disposed high above the ground, e.g., on a tower of a petrochemical plant; located in close proximity to moving parts of a machine, or any other location that restricts a person desiring to read the diagnostic gauge from safely and easily approaching the diagnostic gauge.

The necessity of a person attempting to read the diagnostic gauge to get as close as possible to the diagnostic gauge is increased during times when little or no light is present, e.g., at night, when overhead lighting, either natural, e.g., sunlight, or artificial light, is unavailable, or when the diagnostic gauges are placed in obstructed areas. Generally, a diagnostic gauge cannot be accurately read at distances greater than about four feet when little or no light is present. Under these conditions, the person must taken special precautions to approach the diagnostic gauge, e.g., put on special clothing to enter radioactive areas or read the diagnostic gauges in inclement weather; or climb ladders to reach the diagnostic gauge disposed high above the ground. Further, many times locating a diagnostic gauge desired to be read in low or no light conditions is very difficult.

Prior attempts to address the problem of reading diagnostic gauges in low or no light have been directed at adding either external lighting or internal lighting to the diagnostic gauge. External lighting requires leaving overhead lights on at all times or placing additional lighting focused on the diagnostic gauge. Internal lighting requires wiring the diagnostic gauge with electrical circuitry and/or batteries, to illuminate the diagnostic dial, or face. Both of these approaches increase the cost of the diagnostic gauge and/or the construction and maintenance of the additional wiring and equipment. In another prior attempt, the face and markings on the face of the diagnostic gauge utilize contrasting colors. For example, in one prior attempt, the face is white and the markings are black. In another attempt, the face is black in the markings are white. Neither of these prior approaches sufficiently assist a person to read the diagnostic gauge from a distance under low and no light conditions.

Accordingly, prior to the development of the present invention, there has been no industrial diagnostic gauge that can be read in low or no light conditions, method of reading an industrial diagnostic gauge in low or no light conditions, and method of manufacturing an industrial diagnostic gauge, which: do not require the presence of an electrical light source located internally within, or externally in close proximity to, the industrial diagnostic gauge; do not substantially increase the cost of the industrial diagnostic gauge; permit the industrial diagnostic gauge to be easily located; and permit the industrial diagnostic gauge to be read from a distance. Therefore, the art has sought an industrial diagnostic gauge that can be read in low or no light conditions, method of reading an industrial diagnostic gauge in low or no light conditions, and method of manufacturing an industrial diagnostic gauge, which: do not require the presence of an electrical light source located internally within, or externally in close proximity to, the industrial diagnostic gauge; do not substantially increase the cost of the industrial diagnostic gauge; permit the industrial diagnostic gauge to be easily located; and permit the industrial diagnostic gauge to be read from a distance.

SUMMARY OF INVENTION

In accordance with the invention the foregoing advantages have been achieved through the present industrial diagnostic gauge comprising: a housing; a diagnostic member; a face, wherein the face includes at least one luminescent material; and at least one hand operatively associated with the diagnostic member.

In a further embodiment of the industrial diagnostic gauge, the at least one hand may include at least one reflective material. In another embodiment of the industrial diagnostic gauge, the face may include at least one face marking. In still another embodiment of the industrial diagnostic gauge, the at least one face marking may include at least on reflective material. In an additional embodiment of the industrial diagnostic gauge, the industrial diagnostic gauge may measure pressure. In still another embodiment of the industrial diagnostic gauge, the industrial diagnostic gauge may measure temperature.

In accordance with the invention the foregoing advantages have also been achieved through the present industrial diagnostic gauge comprising: a housing; a diagnostic member; a face having at least one marking, wherein the at least one face marking includes at least one reflective material; and at least one hand operatively associated with the diagnostic member.

In a further embodiment of the industrial diagnostic gauge, the at least one hand may include at least one reflective material. In another embodiment of the industrial diagnostic gauge, the face may include at least one luminescent material. In an additional embodiment of the industrial diagnostic gauge, the industrial diagnostic gauge may measure pressure. In still another embodiment of the industrial diagnostic gauge, the industrial diagnostic gauge may measure temperature.

In accordance with the invention the foregoing advantages have also been achieved through the present industrial diagnostic gauge comprising: a housing; a diagnostic member; a face; and at least one hand operatively associated with the diagnostic member, wherein the at least one hand includes at least one reflective material.

In a further embodiment of the industrial diagnostic gauge, the face may include at least one luminescent material. In another embodiment of the industrial diagnostic gauge, the face may include at least one face marking. In an additional embodiment of the industrial diagnostic gauge, the industrial diagnostic gauge may measure pressure. In still another embodiment of the industrial diagnostic gauge, the industrial diagnostic gauge may measure temperature.

In accordance with the invention the foregoing advantages have also been achieved through the present industrial diagnostic gauge comprising: a housing; a diagnostic member; a face, wherein the face includes at least one reflective material; and at least one hand operatively associated with the diagnostic member.

In a further embodiment of the industrial diagnostic gauge, the at least one hand may include at least one luminescent material. In another embodiment of the industrial diagnostic gauge, the face may include at least one face marking. In an additional embodiment of the industrial diagnostic gauge, the at least one face marking may include at least one luminescent material.

In accordance with the invention the foregoing advantages have also been achieved through the present industrial diagnostic gauge comprising: a housing; a diagnostic member; a face having at least one face marking, wherein the at least one marking includes at least one luminescent material; and at least one hand operatively associated with the diagnostic member.

In a further embodiment of the industrial diagnostic gauge, the at least one hand may include at least one luminescent material. In another embodiment of the industrial diagnostic gauge, the face may include at least one reflective material.

In accordance with the invention the foregoing advantages have also been achieved through the present industrial diagnostic gauge comprising: a housing; a diagnostic member; a face; and at least one hand operatively associated with the diagnostic member, wherein the at least one hand includes at least one luminescent material.

In a further embodiment of the industrial diagnostic gauge, the face may include at least one marking. In an additional embodiment of the industrial diagnostic gauge, the at least one face marking may include at least one luminescent material. In another embodiment of the industrial diagnostic gauge, the face may include at least one reflective material.

In accordance with the invention, the foregoing advantages have also been achieved through the present method of reading a diagnostic gauge in low or no light conditions comprising the steps of: providing an industrial diagnostic gauge having a housing, a diagnostic member, a face, and at least one hand, wherein the face includes at least one face marking having at least one reflective material; reflecting light off of the at least one face marking; and identifying the position of the at least one hand relative to the at least one face marking.

In a further embodiment of the method of reading a diagnostic gauge in low light conditions may include shining light onto the at least one face marking from a position located a distance away from the industrial diagnostic gauge.

In accordance with the invention, the foregoing advantages have also been achieved through the present method of reading a diagnostic gauge in low or no light conditions comprising the steps of: providing an industrial diagnostic gauge having a housing, a diagnostic member, a face, and at least one hand, wherein the hand includes at least one reflective material; reflecting light off of the at least one hand; and identifying the position of the at least one hand.

In a further embodiment of the method of reading a diagnostic gauge in low light conditions may include shining light onto the at least one hand from a position located a distance away from the industrial diagnostic gauge.

In accordance with the invention, the foregoing advantages have also been achieved through the present method of manufacturing an industrial diagnostic gauge comprising the steps of: applying at least one luminescent material to a face of the industrial diagnostic gauge; connecting the face to a diagnostic member; and disposing the diagnostic member and face within a housing.

In another embodiment of the method of manufacturing an industrial diagnostic gauge, the at least one luminescent material is applied to the face by coating the face with the luminescent material. In a further embodiment of the method of manufacturing an industrial diagnostic gauge, the at least one luminescent material is applied to the face by combining the luminescent material with at least one clear paint to form a luminescent paint and coating the face with the luminescent paint. In an additional embodiment of the method of manufacturing an industrial diagnostic gauge, the face is coated with the luminescent paint by spraying. In still another embodiment of the method of manufacturing an industrial diagnostic gauge, the at least one clear paint is clear acrylic paint. In a further embodiment of the method of manufacturing an industrial diagnostic gauge, the at least one luminescent material is applied to the face of the diagnostic member by combining the luminescent material with a material that forms the face.

In accordance with the invention, the foregoing advantages have also been achieved through the present method of manufacturing an industrial diagnostic gauge comprising the steps of: applying at least one reflective material to a hand of the industrial diagnostic gauge; connecting the hand to a diagnostic member; and disposing the diagnostic member and the hand within a housing.

In accordance with the invention, the foregoing advantages have also been achieved through the present method of manufacturing an industrial diagnostic gauge comprising the steps of: applying at least one reflective material to a face of the industrial diagnostic gauge; connecting the face to a diagnostic member; and disposing the diagnostic member and face within a housing.

In accordance with the invention, the foregoing advantages have also been achieved through the present method of manufacturing an industrial diagnostic gauge comprising the steps of: applying at least one luminescent material to a hand of the industrial diagnostic gauge; connecting the hand to a diagnostic member; and disposing the diagnostic member and the hand within a housing.

In accordance with the invention, the foregoing advantages have also been achieved through the present method of manufacturing an industrial diagnostic gauge comprising the steps of: applying at least one reflective material to at least one face marking on a face of the industrial diagnostic gauge; connecting the face to a diagnostic member; and disposing the diagnostic member and the face within a housing.

In accordance with the invention, the foregoing advantages have also been achieved through the present method of manufacturing an industrial diagnostic gauge comprising the steps of: applying at least one luminescent material to at least one face marking on a face of the industrial diagnostic gauge; connecting the face to a diagnostic member; and disposing the diagnostic member and the face within a housing.

In accordance with the invention the foregoing advantages have also been achieved through the present industrial diagnostic gauge comprising: a housing having at least one housing marking, wherein the at least one housing marking includes at least one luminescent material; a diagnostic member; a face, and at least one hand operatively associated with the diagnostic member.

A further feature of the industrial diagnostic gauge is that the at least one hand may include at least one reflective material. Another feature of the industrial diagnostic gauge is that the at least one hand may include at least one luminescent material. An additional feature of the industrial diagnostic gauge is that the face may include at least one reflective material. Still another feature of the industrial diagnostic gauge is that the face may include at least one face marking. A further feature of the industrial diagnostic gauge is that the at least one face marking may include at least one luminescent material. Another feature of the industrial diagnostic gauge is that the face may include at least one luminescent material. An additional feature of the industrial diagnostic gauge is that the at least one face marking may include at least one reflective material.

In accordance with the invention the foregoing advantages have also been achieved through the present industrial diagnostic gauge comprising: a housing having at least one housing marking, wherein the at least one housing marking includes at least one reflective material; a diagnostic member; a face; and at least one hand operatively associated with the diagnostic member.

A further feature of the industrial diagnostic gauge is that the at least one hand may include at least one reflective material. Another feature of the industrial diagnostic gauge is that the at least one hand may include at least one luminescent material. An additional feature of the industrial diagnostic gauge is that the face may include at least one reflective material. Still another feature of the industrial diagnostic gauge is that the face may include at least one face marking. A further feature of the industrial diagnostic gauge is that the at least one face marking may include at least one luminescent material. Another feature of the industrial diagnostic gauge is that the face may include at least one luminescent material. An additional feature of the industrial diagnostic gauge is that the at least one face marking may include at least one reflective material.

In accordance with the invention the foregoing advantages have been achieved through the present method of reading an industrial diagnostic gauge in low or no light conditions, comprising the steps of: providing an industrial diagnostic gauge having a housing, a diagnostic member, a face, and at least one hand, wherein the housing includes at least one housing marking having at least one reflective material; reflecting light off of the at least one housing marking; and identifying the position of the at least one hand relative to the at least one housing marking.

A further feature of the method of reading an industrial diagnostic gauge in low or no light conditions is that the at least one hand may include at least one reflective material and light is reflected of the at least one hand.

In accordance with the invention the foregoing advantages have also been achieved through the present industrial diagnostic gauge comprising: a housing; a retaining ring having at least one housing marking, wherein the at least one housing marking includes at least one luminescent material; a diagnostic member; a face, and at least one hand operatively associated with the diagnostic member.

A further feature of the industrial diagnostic gauge is that the at least one hand may include at least one reflective material. Another feature of the industrial diagnostic gauge is that the at least one hand may include at least one luminescent material.

In accordance with the invention the foregoing advantages have also been achieved through the present industrial diagnostic gauge comprising: a housing; a retaining ring having at least one housing marking, wherein the at least one housing marking includes at least one reflective material; a diagnostic member; a face, and at least one hand operatively associated with the diagnostic member.

A further feature of the industrial diagnostic gauge is that the at least one hand may include at least one reflective material. Another feature of the industrial diagnostic gauge is that the at least one hand may include at least one luminescent material.

In accordance with the invention the foregoing advantages have also been achieved through the present industrial diagnostic gauge comprising: a housing; at least one clip having at least one housing marking, wherein the at least one housing marking includes at least one reflective material; a diagnostic member; a face; and at least one hand operatively associated with the diagnostic member.

A further feature of the industrial diagnostic gauge is that the at least one hand may include at least one reflective material. Another feature of the industrial diagnostic gauge is that the at least one hand may include at least one luminescent material.

In accordance with the invention the foregoing advantages have also been achieved through the present industrial diagnostic gauge comprising: a housing; at least one clip having at least one housing marking, wherein the at least one housing marking includes at least one luminescent material; a diagnostic member; a face; and at least one hand operatively associated with the diagnostic member.

A further feature of the industrial diagnostic gauge is that the at least one hand may include at least one reflective material. Another feature of the industrial diagnostic gauge is that the at least one hand may include at least one luminescent material.

The industrial diagnostic gauge that can be read in low or no light conditions, method of reading a diagnostic gauge in low or no light conditions, and method of manufacturing an industrial diagnostic gauge have the advantages of: not requiring the presence of an electrical light source located internally within, or externally in close proximity to, the industrial diagnostic gauge; not substantially increasing the cost of the industrial diagnostic gauge; permitting the industrial diagnostic gauge to be easily located; and permitting the industrial diagnostic gauge to be read from a distance.

While the invention will be described in connection with the preferred embodiment, it will be understood that it is not intended to limit the invention to that embodiment. On the contrary, it is intended to cover all alternatives, modifications, and equivalents, as may be included within the spirit and scope of the invention as defined by the appended claims.

DETAILED DESCRIPTION AND SPECIFIC EMBODIMENTS

The present invention relates to industrial diagnostic gauges, or diagnostic gauges, that can be read under low, or no light conditions, and can be read at distances up to at least 10 feet. Diagnostic gauges are herein defined as pressure gauges, differential gauges, bi-metal thermometers, glass industrial thermometers, surface thermometers, gas actuated thermometers, vapor tension thermometers, level gauges, or any other diagnostic gauge utilized in industrial applications.

Figure 1:
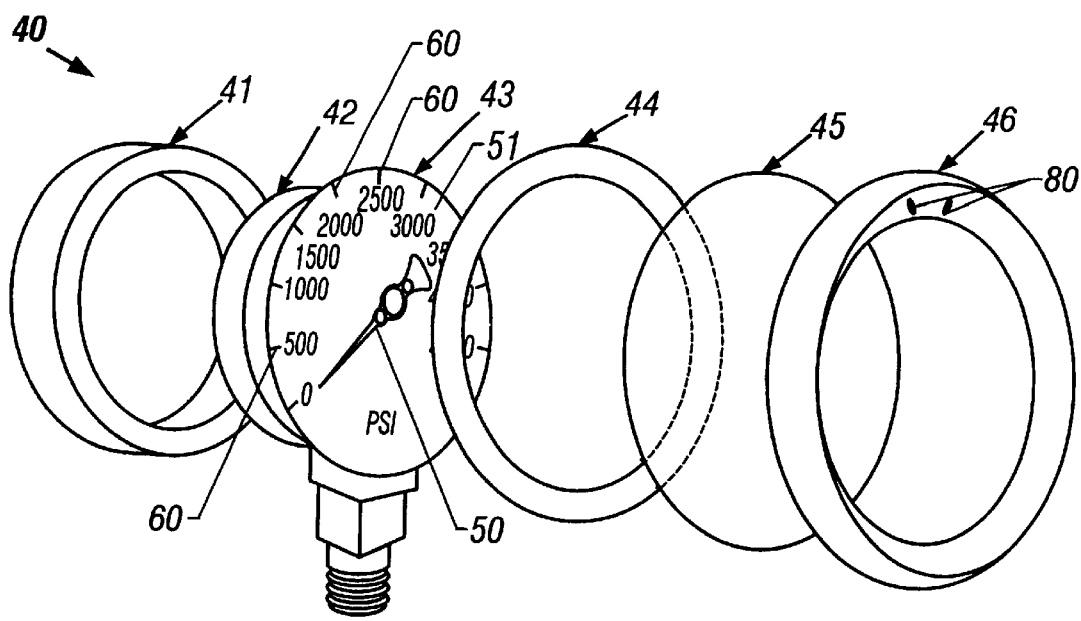
FIG. 1 is a perspective exploded view of an industrial diagnostic gauge of the present invention.
Figure 2:
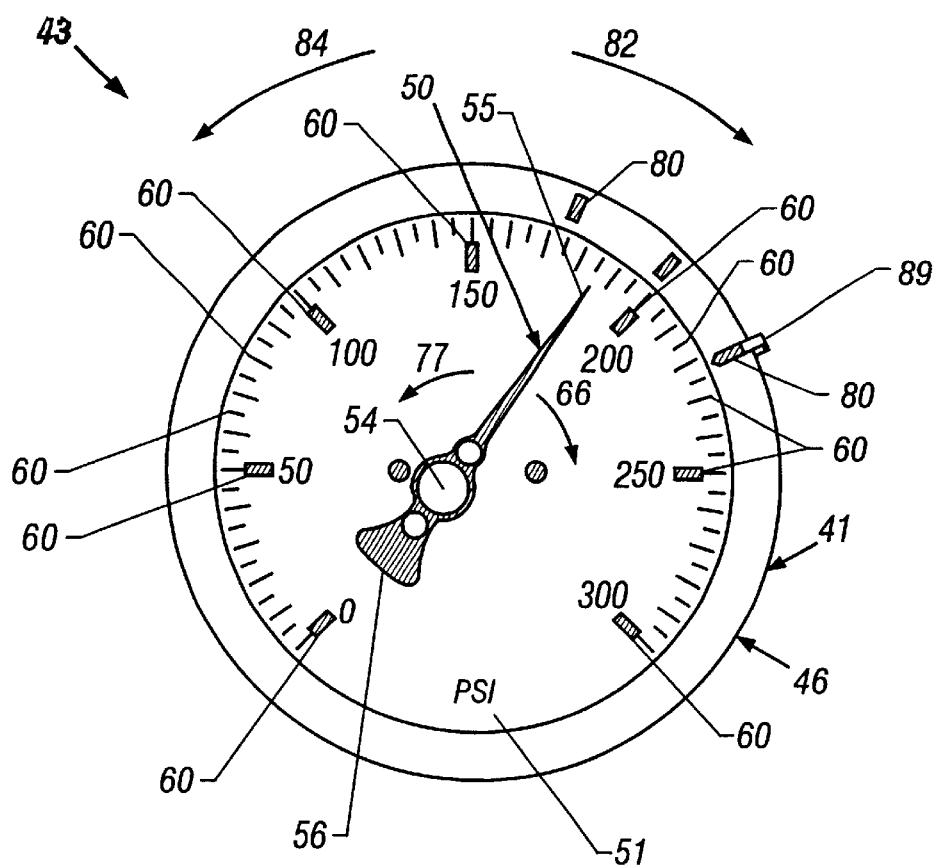
FIG. 2 is a front view of the face of the industrial diagnostic gauge shown in FIG. 1.

Referring now to FIGS. 1 and 2, broadly, an industrial diagnostic gauge 40 includes a housing 41, a diagnostic member 42, a face 43, and at least on needle, or hand, 50. Face 43 includes a top surface 51.

Hand 50 is operatively associated with diagnostic member 42. Accordingly, as diagnostic member 42 is activated, e.g., the pressure or temperature increases or decreases, the at least one hand 50 moves, or points, to quantitatively indicate the level of whatever the industrial diagnostic gauge is designed to measure, e.g., the pressure or temperature. Preferably, the at least one hand 50 point relative to at least one face marking 60 disposed on face 43. In the embodiment shown in FIGS. 1 and 2, hand 50 is permitted to move in a clockwise direction (arrow 66) and a counter-clockwise direction (arrow 77).

Industrial diagnostic gauge 40 may also include a gasket 44, a clear window 45, and a retaining ring 46. Housing 41, diagnostic member 42, face 43, gasket 44, clear window 45, and retaining ring 46 may be any shape and manufactured out of any material desired or necessary depending upon the application in which the diagnostic gauge 40 will be utilized. As shown in FIGS. 1 and 2, diagnostic member 42 measures pressure. Therefore, diagnostic gauge 40 shown in FIGS. 1 and 2 is a pressure gauge. It is to be understood that diagnostic member 42 may be any industrial diagnostic device known to persons of ordinary skill in the art. For example, diagnostic member 42 may measure temperature. In these embodiments, the diagnostic gauge is a temperature gauge.

As mentioned above, disposed along top surface 51 of face 43 is preferably at least one face marking 60. As shown in FIGS. 1 and 2, numerous markings 60 are disposed along the perimeter of face 43. Preferably, markings 60 are incremental. In other words, each face marking 60 represents a specific, and identical, increase or decrease in the reading provided by the diagnostic member 42, e.g., 10 degrees or 5 psi (FIG. 2). Markings 60 may be printed on, or affixed to, the face 43 using any method or device known to persons skilled in the art. In one embodiment, markings 60 are formed using paint. In another embodiment, markings 60 are formed using stickers. In still another embodiment, markings 60 are formed using luminescent materials that glow, or illuminate, without the presence of external or internal light sources. While numerous luminescent materials are contemplated to be acceptable, one suitable luminescent material is NIGHTLIGHT20™, a phosphorescent powder sold by DORAK International Corporation. In this embodiment, direct light or ambient light charges, or energizes, the luminescent material which then glows or illuminates in low light and no light conditions permitting a person to read the markings at distances of at least about 10 feet without assistance from internal or external lighting.

In a preferred embodiment, markings 60 are formed using reflective materials that are capable of reflecting substantially all light that shines onto the reflective materials. Examples include reflective paint, stickers, tape, or other reflective adhesives such as vinyl reflective strips made-and sold by 3M Corporation. In this embodiment, the reflective materials permit a person to accurately read the markings at distances up to about 50 feet or more in low or no light conditions when the person shines a light, e.g., a flashlight, on the markings 60.

As mentioned above, face 43 may be constructed out of any material desired or necessary depending upon the application in which the diagnostic gauge 40 will be utilized. In one embodiment, top surface 51 may include reflective materials as discussed above. In a preferred embodiment, face 43 includes a luminescent material evenly distributed along top surface 51 of face 43. Alternatively, the luminescent material may be incorporated into the material used to form the top surface 51 of face 43. For example, face 43, and top surface 51, may be manufactured using a plastic extrusion process in which the luminescent material is incorporated into the plastic prior to extruding the plastic into the shape of face 43. In one embodiment, top surface 51 of face 43 is coated with a luminescent paint that is formed by combining NIGHTLIGHT20™ luminescent powder with clear acrylic paint. The luminescent paint is distributed evenly along top surface 51 by any method known to persons skilled in the art, e.g., spraying, or dipping, face 43 with, or into, the luminescent paint. In one embodiment, two parts luminescent powder combined with five parts clear acrylic paint has been found to provide the desired results. As mentioned above, the luminescent material permits a person to read the industrial diagnostic gauge from distances of at least about 10 feet without assistance from internal or external light sources. Additionally, the luminescent material permits a person to determine the location of an industrial diagnostic gauge 40 in low or no light conditions from distances up to about 100 feet away. This feature is beneficial in large industrial plants having numerous industrial diagnostic gauges located throughout the plant at varying levels.

Hand 50 may also include at least one luminescent material and/or at least one reflective material. Hand 50 is operatively associated with diagnostic member 42 at connection 54 which permits hand 50 to move as discussed above. In one embodiment, hand 50 includes two ends, an indicator end 55 and a balance end 56, disposed opposite of each other relative to connection 54. Indicator end 55 is used to read the diagnostic gauge 40. In one embodiment, indicator end 55 aligns with, or in close proximity with, at least one face marking 60. Balance end 56 may offset the weight of indicator end 55, and thus, provide balance to hand 50. Alternatively, balance end 56 may be operatively associated with diagnostic member 42, i.e., connection 54 is located at balance end 56. In one embodiment, only indicator end 55 of hand 50 includes the at least one luminescent material and/or at least one reflective material. In a preferred embodiment, the indicator end 55 of hand 50 includes at least one reflective material, thereby permitting the position of indicator end 55 of hand 50 to be easily determined by shining light, e.g., from a flashlight, on the indicator end 55. Accordingly, industrial diagnostic gauge 40 may be accurately read, from varying distances.

In one specific embodiment, industrial diagnostic gauge 40 includes a face 43 having at least one luminescent material, at least one face marking 60 having at least one reflective material, and at least one hand 50 having at least one reflective material. In this preferred embodiment, face 43 contrasts sharply with the at least one face marking 60 and the at least one hand 50. Accordingly, industrial diagnostic gauge 40 may be easily located, and accurately read, by a person. Further, after the diagnostic gauge 40 is manufactured, no additional maintenance to the face 43, markings 60, or hand 50 is required. Moreover, no additional wiring is required assist a person to accurately read the industrial diagnostic gauge 40.

In another specific embodiment, housing 41, retaining ring 46, or bracket, or clip, 89 (FIG. 2) may include at least one housing marking 80. Housing marking 80 may be disposed on one or more of housing 41, retaining ring, 46 or clip 89. It is to be understood that in some embodiments, housing 41 and retaining ring 46 may be integral.

As shown in FIGS. 1 and 2, two housing markings 80 are disposed along the perimeter of housing 41/retaining ring 46 (FIG. 2), thereby indicating a range. Also shown in FIG. 1, one housing marking 80 is disposed on clip 89. In one specific embodiment, numerous housing markings 80 may be disposed along the perimeter of housing 41, retaining ring 46, or on more than one clip 89 thereby indicating incremental differences between each housing marking 80 as discussed in greater detail above with reference to markings 60 disposed along face 43.

Housing markings 80 may be printed on, or affixed to, housing 41, retaining ring 46, or clip 89 using any method or device known to persons skilled in the art. In one embodiment, housing markings 80 are formed using paint. In another embodiment, housing markings 80 are formed using stickers. In still another embodiment, housing markings 80 are formed using luminescent materials discussed in greater detail above. In another specific embodiment, housing markings 80 are formed from reflective materials discussed in greater detail above. In this embodiment, the position of indicator end 55 of hand 50 to be easily determined by shining light, e.g., from a flashlight, on housing marking 80.

While housing markings 80 may be permanent or non-removable, or removable so that housing markings 80 may be adjusted or customized as desired or necessary to indicate a desired range, in a preferred embodiment, housing markings 80 are permanent and housing 41 or retaining ring 46 is rotatable in the directions indicated by arrows 82 and 84. In another embodiment, housing marking 80 on clip 89 is permanent and clip 89 is moveable, or slidable, along the perimeter of face 43 in the direction of arrows 82, 84. Therefore, the range indicated by housing markings 80 in FIGS. 1 and 2 can be easily adjusted.

The industrial diagnostic gauges 40 of the present invention may be manufacturing by applying at least one luminescent material to one or more of face 43, face marking 60, housing marking 80 and/or hand 50. Face 43 is connected to diagnostic member 42 and hand 50 is operatively associated with diagnostic member 42. Diagnostic member 42 is then disposed within housing 41. In the embodiment shown in FIG. 1, diagnostic member 42 is disposed between housing 41 and clear window 45. Retaining ring 46 is then connected to housing 41 using any method or device known to persons skilled in the art, e.g., screws, bolts, threaded connectors, etc., to capture diagnostic member 42 and clear window 45 between housing 41 and retaining ring 46. Water or other liquid (not shown) may also be disposed between face 43 of diagnostic member 42 and clear window 45.

Luminescent material may be applied to one or more face 43, face marking 60, housing marking 80 and/or hand 50. Alternatively, reflective material may be applied to one or more of face 43, face marking 60, housing marking 80, and/or hand 50. In one specific embodiment, luminescent material is applied to face 43 and reflective material is applied to hand 50 and to face marking 60 disposed on face 43. In another specific embodiment, reflective material is applied to housing marking 80 on housing 41. The luminescent material and the reflective material may be applied in any manner known to persons skilled in the art of applying these materials. For example, the luminescent material and the reflective material may be applied as discussed in greater detail above.

It is to be understood that the invention is not limited to the exact details of construction, operation, exact materials, or embodiments shown and described, as obvious modifications and equivalents will be apparent to one skilled in the art. For example, the diagnostic gauge may include reflective materials associated only with one of either the hand, face marking, housing marking, or face. Alternatively, the diagnostic gauge may include luminescent materials associated only with one of either the face, hand, housing marking, or face marking. In another embodiment, the luminescent materials and the reflective materials may be associated with the face, hand, housing marking and face marking in any other combination that facilitates accurate reading of the industrial diagnostic gauge in low or no light conditions from varying distances. In still another embodiment, hand may move in a horizontal or a vertical direction. Accordingly, the invention is therefore to be limited only by the scope of the appended claims.

What is claimed:

1. An industrial diagnostic gauge comprising:
   a housing having at least one housing marking, wherein the at least one housing marking includes at least one reflective material;
   a diagnostic member;
   a face; and
   at least one hand operatively associated with the diagnostic member.

2. The industrial diagnostic gauge of claim 1, wherein the at least one hand includes at least one reflective material.

3. The industrial diagnostic gauge of claim 1, wherein the at least one hand includes at least one luminescent material.

4. The industrial diagnostic gauge of claim 1, wherein the face includes at least one reflective material.

5. The industrial diagnostic gauge of claim 1, wherein the face includes at least one luminescent material.

6. The industrial diagnostic gauge of claim 5, wherein the at least one hand includes at least one reflective material.

7. The industrial diagnostic gauge of claim 1, wherein the face includes at least one face marking having at least one reflective material.

8. The industrial diagnostic gauge of claim 1, wherein the face includes at least one face marking having at least one luminescent material.

9. An industrial diagnostic gauge comprising:
   a housing;
   a retaining ring having at least one housing marking, wherein the at least one housing marking includes at least one reflective material;
   a diagnostic member;
   a face, and
   at least one hand operatively associated with the diagnostic member.

10. The industrial diagnostic gauge of claim 9, wherein the at least one hand includes at least one reflective material.

11. The industrial diagnostic gauge of claim 9, wherein the at least one hand includes at least one luminescent material.

12. An industrial diagnostic gauge comprising:
    a housing;
    at least one clip having at least one housing marking, wherein the at least one housing marking includes at least one reflective material;
    a diagnostic member;
    a face; and
    at least one hand operatively associated with the diagnostic member.

13. The industrial diagnostic gauge of claim 12, wherein the at least one hand includes at least one reflective material.

14. The industrial diagnostic gauge of claim 12, wherein the at least one hand includes at least one luminescent material.

15. A method of reading an industrial diagnostic gauge in low or no light conditions, comprising the steps of:

providing an industrial diagnostic gauge having a housing, a diagnostic member, a face, and at least one hand, wherein the housing includes at least one housing marking having at least one reflective material;

reflecting light off of the at least one housing marking; and identifying the position of the at least one hand relative to the at least one housing marking.

16. The method of claim 15, wherein the at least one hand includes at least one reflective material and light is reflected of the at least one hand.

17. The industrial diagnostic gauge of claim 9, wherein the face includes at least one luminescent material.

18. The industrial diagnostic gauge of claim 17, wherein the at least one hand includes at least on reflective material.

19. The industrial diagnostic gauge of claim 12, wherein the face includes at least one luminescent material.

20. The industrial diagnostic gauge of claim 19, wherein the at least one hand includes at least one reflective material.

* * * * *